US00PP10214P

United States Patent [19]

Wain

[11] Patent Number: Plant 10,214

[45] Date of Patent: Jan. 27, 1998

[54] CHRYSANTHEMUM PLANT NAMED 'EGRET'

[75] Inventor: Peter Wain, Portsmouth, United Kingdom

[73] Assignee: Cleangro Ltd., Chichester, United Kingdom

[21] Appl. No.: 754,069

[22] Filed: Nov. 20, 1996

[51] Int. Cl.[6] ..... A01H 5/00

[52] U.S. Cl. ..... Plt./77

[58] Field of Search ..... Plt./78, 77

*Primary Examiner*—Howard J. Locker

*Attorney, Agent, or Firm*—C. A. Whealy

[57] ABSTRACT

A distinct cultivar of Chrysanthemum plant named 'Egret', characterized by its tall, vigorous, mounded and upright growth habit; decorative-type inflorescences; cream-colored to white ray florets; small, but numerous inflorescences per plant; numerous ray florets per inflorescence; and good garden performance.

2 Drawing Sheets

1

The present invention relates to a new and distinct cultivar of garden Chrysanthemum plant, botanically known as *Dendranthema grandiflora* and referred to by the cultivar name Egret.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the proprietary selection 10/GM/94 as the female, or seed, parent with the commercial cultivar Empire Chablis (U.S. Plant Pat. No. 8,986) as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Egret'. These characteristics in combination distinguish 'Egret' as a new and distinct cultivar:

1. Tall, vigorous, mounded and upright growth habit.
2. Decorative-type inflorescences.
3. Cream-colored to white ray florets.
4. Small, but numerous inflorescences per plant.
5. Numerous ray florets per inflorescence.
6. Good garden performance.

The cultivar Egret has not been observed under all possible environmental conditions. The phenotype may vary somewhat with variations in environment such as temperature, daylength and light intensity, without , however, any variance in genotype.

In side-by-side comparisons in Chichester, West Sussex, United Kingdom, under commercial practice, plants of the new Chrysanthemum have lighter green foliage, more ray florets per inflorescence and flower earlier than plants of the female parent, the proprietary selection 10/GM/4. In addition, plants of the new Chrysanthemum have decorative-type inflorescences with cream-colored to white ray florets whereas plants of the proprietary selection 10/GM/4 have daisy-type inflorescences with yellow ray florets. In the same comparisons, plants of the new Chrysanthemum are more compact and fuller, have lighter green foliage and smaller inflorescences, and flower later than plants of the male parent, the commercial cultivar Empire Chablis. In addition, plants of the new Chrysanthemum have cream-colored to white ray florets whereas ray florets of plants of the cultivar Empire Chablis are white.

2

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Egret' with five cuttings in the container.

The second photograph comprises a close-up view of typical inflorescences. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C, day temperatures ranging between 20 and 30C, and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Egret.

Commercial classification: Garden chrysanthemum.

Parentage:

*Female, or seed, parent.*—*Dendranthema grandiflora* proprietary selection 10/GM94.

*Male, or pollen, parent.*—*Dendranthema grandiflora* cultivar. Empire Chablis (U.S. Plant Pat. No. 8,986).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Mounded plant shape, uniform, vigorous and tall, stems upright. Freely branching.

*Plant height.*—About 30 cm.

*Quantity of lateral branches after removal of apical meristem.*—About 5.

*Foliage description.*—Number of leaves per plant: About 110. Number of leaves per lateral branch: About 22. Leaf arrangement: Alternate. Leaf size, fully expanded: Length: 5.5 to 7 cm. Width: 4.5 to 5 cm. Leaf apex: Mucronate. Leaf base: Truncate/attenuate. Leaf margin: Palmately lobed. Leaf texture: Leathery, fleshy and smooth. Veins prominent on abaxial surface. Abaxial surface slightly pubsecent. Petiole length: 1 to 1.5 cm. Color: Young foliage adaxial surface: 137C. Young foliage abaxial surface: 138B. Fully expanded foliage adaxial surface: 137C. Fully expanded foliage abaxial surface: 138B. Venation abaxial surface: 138B. Venation adaxial surface: 138B. Petiole: Edge: 137C. Center: 138B.

Inflorescence description:

*Appearance.*—Decorative-type inflorescence form. Inflorescences borne on terminals above foliage, arising from leaf axils. Ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 56 days later. Flowers last about 3 weeks on the plant.

*Quantity of inflorescences.*—About 10 inflorescences per flowering stem.

*Inflorescence size.*—Diameter: About 3.5 cm. Depth (height): 1 to 2 cm.

*Opening inflorescences.*—Bud shape: Spherical. Bud size: Length: About 7.5 to 10 mm. Width: About 1 cm. Bud color: 10C.

*Ray florets.*—Shape: Obovate. Size: Length: 1.25 to 1.75 cm. Width: 5 to 10 mm. Apex: Mucronate. Base: Acute. Margin: Entire. Texture: Smooth and glabrous. Number of ray florets per inflorescence: 175 to 185. Color: When opening: 10C. Mature, adaxial surface: 155C. Mature, abaxial surface: 155D. Fading to: 155B.

*Disc florets.*—None present.

*Peduncle.*—Aspect: Slender, medium to weak. Length: 3.5 to 5.5 cm. Texture: Pubescent. Color: 138B.

*Sepals.*—Shape: Linear. Calyx size: 1 to 1.5 cm. Apex: Acute. Margin: Entire. Texture: Leathery and pubescent. Quantity per inflorescence: About 25. Color: Adaxial surface: 141C. Abaxial surface: 138B/138C.

*Reproductive organs.*—Androecium: Not present on ray florets. Gynoecium: Style length: 2 to 4 mm. Style color: 8D. Stigma color: 8B.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Egret', as illustrated and described.

* * * * *

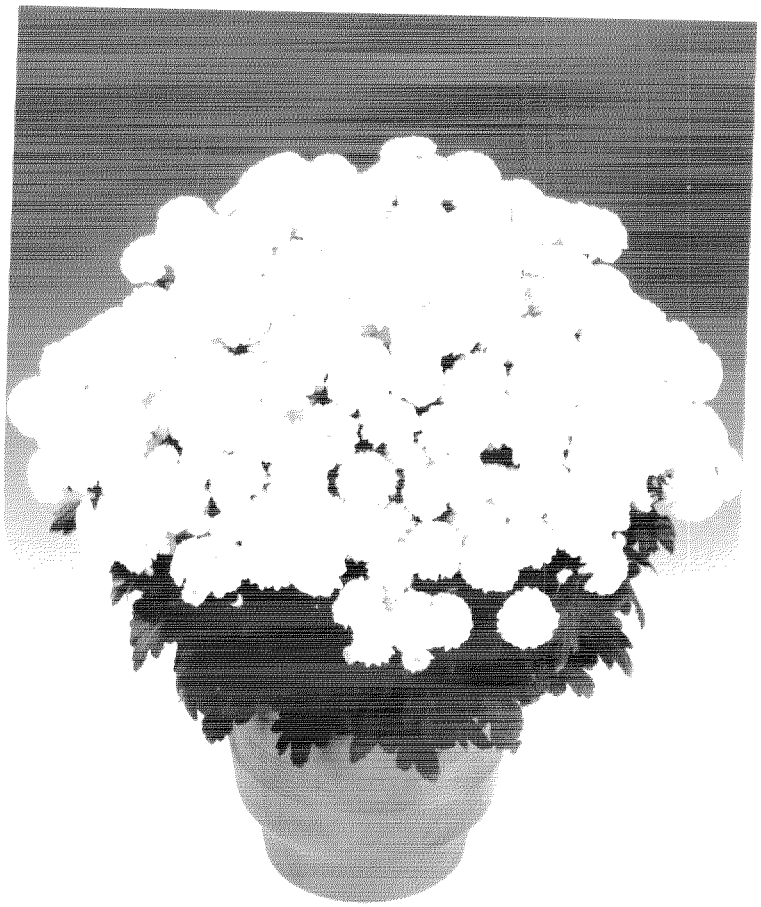

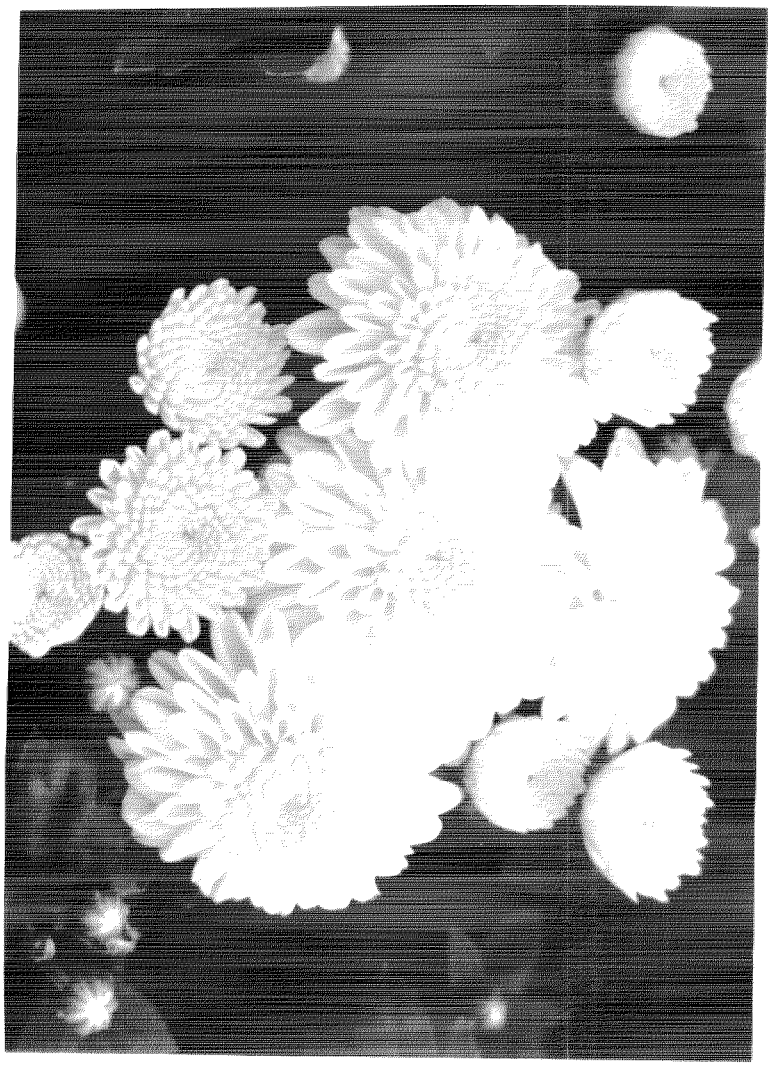

UNITED STATES PATENT AND TRADEMARK OFFICE

CERTIFICATE OF CORRECTION

PATENT NO. : Plant 10,214
DATED : January 27, 1998
INVENTOR(S) : Peter Wain

It is certified that error appears in the above-indentified patent and that said Letters Patent is hereby corrected as shown below:

Column 1, line 38, change "without ," to -- without. --.
Column 2, line 37, change "10/GM94" to -- 10/GM/94 --.

Signed and Sealed this

Second Day of February, 1999

*Attest:*

*Attesting Officer*

*Acting Commissioner of Patents and Trademarks*